United States Patent
Liu et al.

(10) Patent No.: US 12,369,627 B2
(45) Date of Patent: Jul. 29, 2025

(54) ULTRASONIC ATOMIZING SHEET FULL-WAVE DRIVE CIRCUIT AND ULTRASONIC ELECTRONIC CIGARETTE

(71) Applicant: CHINA TOBACCO HUNAN INDUSTRIAL CO., LTD., Hunan (CN)

(72) Inventors: Jianfu Liu, Hunan (CN); Kejun Zhong, Hunan (CN); Xiaoyi Guo, Hunan (CN); Xinqiang Yin, Hunan (CN); Jianhua Yi, Hunan (CN); Yuebin Deng, Hunan (CN)

(73) Assignee: CHINA TOBACCO HUNAN INDUSTRIAL CO., LTD., Hunan (CN)

( * ) Notice: Subject to any disclaimer, the term of this patent is extended or adjusted under 35 U.S.C. 154(b) by 711 days.

(21) Appl. No.: 17/777,016

(22) PCT Filed: Nov. 26, 2020

(86) PCT No.: PCT/CN2020/131751
§ 371 (c)(1),
(2) Date: May 13, 2022

(87) PCT Pub. No.: WO2021/104370
PCT Pub. Date: Jun. 3, 2021

(65) Prior Publication Data
US 2022/0400747 A1    Dec. 22, 2022

(30) Foreign Application Priority Data

Nov. 26, 2019 (CN) .......................... 201911174090.5
Nov. 26, 2019 (CN) .......................... 201922063769.9
Nov. 26, 2019 (CN) .......................... 201922063798.5

(51) Int. Cl.
A24F 40/05    (2020.01)
A24F 40/10    (2020.01)
(Continued)

(52) U.S. Cl.
CPC .............. *A24F 40/05* (2020.01); *A24F 40/10* (2020.01); *A61M 11/005* (2013.01);
(Continued)

(58) Field of Classification Search
CPC ... A61M 15/001; A61M 11/005; A24F 40/57; A24F 40/50; A24F 40/46; A24F 40/42;
(Continued)

(56) References Cited

U.S. PATENT DOCUMENTS

2017/0027233 A1*  2/2017  Mironov ............... A24F 40/465
2017/0303594 A1*  10/2017 Cameron ............... A61M 15/00
(Continued)

FOREIGN PATENT DOCUMENTS

CN    208079036 U    11/2018
CN    109363245 A    2/2019
(Continued)

OTHER PUBLICATIONS

International Search Report issued in International Application No. PCT/CN2020/131751 dated Feb. 26, 2021, 3 pages.
(Continued)

*Primary Examiner* — Alex B Efta
(74) *Attorney, Agent, or Firm* — MASCHOFF BRENNAN; Michael Mauriel (57) ABSTRACT

Disclosed are a full-wave drive circuit for an ultrasonic atomizing sheet and an ultrasonic electronic cigarette. In an embodiment, the ultrasonic atomizing sheet full-wave drive circuit comprises a power supply module, a microprocessor, a high-frequency square wave generation circuit, an NMOS transistor and a resonance circuit configured to convert, on
(Continued)

the basis of the NMOS transistor, a voltage signal outputted by the high-frequency square wave generation circuit into a full-wave oscillation signal, so as to drive the ultrasonic atomizing sheet to perform full-wave oscillation. A disclosed embodiment has low requirements for a boost module, low loss of the boost module, high power conversion efficiency, small volume, low loss of NMOS transistor and low cost, is easy for debugging, and has high reliability and good atomization effect.

18 Claims, 3 Drawing Sheets

(51) Int. Cl.
  *A24F 40/40*  (2020.01)
  *A61M 11/00*  (2006.01)
  *A61M 15/00*  (2006.01)
  *H03K 17/687*  (2006.01)

(52) U.S. Cl.
  CPC ..... *H03K 17/6872* (2013.01); *H03K 17/6874* (2013.01); *A24F 40/40* (2020.01); *A61M 15/001* (2014.02)

(58) Field of Classification Search
  CPC .......... A24F 40/40; A24F 40/20; A24F 40/10; A24F 40/05; A24F 40/00
  See application file for complete search history.

(56) References Cited

U.S. PATENT DOCUMENTS

2021/0059312 A1*   3/2021   Qiu ..................... A24F 40/57
2021/0186108 A1*   6/2021   Korus ................. A24F 40/465

FOREIGN PATENT DOCUMENTS

| CN | 210670015 U | 6/2020 |
|---|---|---|
| CN | 210670027 U | 6/2020 |
| CN | 211065048 U | 7/2020 |

OTHER PUBLICATIONS

"Discussions on Ultrasonic Atomization Circuit," https://www.sohu.com/a/149441316_774177, 4 pages.
"Dedicated Drive IC for Microporous Ultrasonic Atomizing Sheet," Baidu Library, https://wenku.baidu.com/view/6733a17603020740be1e650e52ea551810a6c9d8.html, 8 pages.

* cited by examiner

ULTRASONIC ATOMIZING SHEET FULL-WAVE DRIVE CIRCUIT AND ULTRASONIC ELECTRONIC CIGARETTE

CROSS REFERENCE TO RELATED APPLICATIONS

This application is a U.S. National Phase application under 35 U.S.C. § 371 of International Application No. PCT/CN2020/131751 filed on Nov. 26, 2020, and claims priority to Chinese Application No. 201911174090.5 filed on Nov. 26, 2019, Chinese Application No. 201922063798.5 filed on Nov. 26, 2019 and Chinese Application No. 201922063769.9 filed on Nov. 26, 2019. The entire contents of these applications are hereby incorporated herein by reference.

FIELD OF THE INVENTION

The present invention particularly relates to a full-wave drive circuit for an ultrasonic atomizing sheet and an ultrasonic electronic cigarette.

BACKGROUND OF THE INVENTION

Drive circuits for an ultrasonic atomizing sheet include half-wave drive circuits and full-wave drive circuits.

Figure 1:
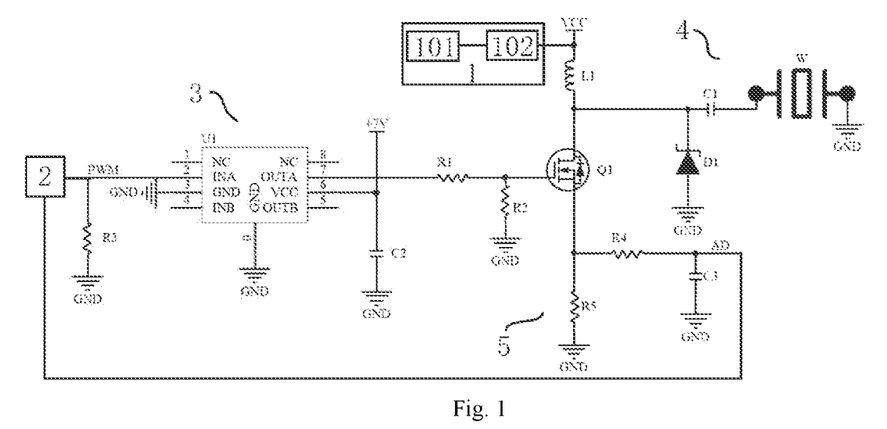
FIG. 1 is a structural diagram of a half-wave drive circuit for an ultrasonic atomizing sheet in the prior art.

As shown in FIG. 1, an existing half-wave drive circuit for the ultrasonic atomizing sheet includes a power module 1, a microprocessor 2, a high-frequency square wave generation circuit 3, an NMOS transistor Q1, a resonance circuit 4, and a current collection circuit 5. The power module 1 includes a battery 101 and a boost module 102; the high-frequency square wave generation circuit 3 includes a resistor R3, a square wave amplifier U1, and a capacitor C2; the resonance circuit 4 includes an inductor L1 and an ultrasonic atomizing sheet W; the current collection circuit 5 includes a resistor R4, a resistor R5 and a capacitor C3; an output end of the microprocessor 2 is electrically connected to an input end of the square wave amplifier U1, the resistor R3 is connected between the input end of the square wave amplifier U1 and the ground, an output end of the square wave amplifier U1 is electrically connected to a gate of the NMOS transistor Q1 through the resistor R1, and the capacitor C2 is connected between a power end of the square wave amplifier U1 and the ground; the gate of the NMOS transistor Q1 is also grounded through the resistor R2, a drain of the NMOS transistor Q1 is electrically connected to a first end of the inductor L1, the battery 101 is electrically connected to a second end of the inductor L1 through the boost module 102, and the ultrasonic atomizing sheet W is connected between the first end of the inductor L1 and the ground; a source of the NMOS transistor Q1 is grounded through the resistor R5, and the source of the NMOS transistor Q1 is also grounded through the resistor R4 and the capacitor C3 in sequence; and the input end of the microprocessor 2 is connected between the resistor R4 and the capacitor C3. A capacitor C1 for reducing or eliminating the interference effect of parasitic capacitance in the ultrasonic atomizing sheet W is also connected between the ultrasonic atomizing sheet W and the first end of the inductor L1, and the first end of the inductor L1 is grounded through a Zener diode D1.

The working principle of the half-wave drive circuit for the ultrasonic atomizing sheet shown in FIG. 1 is: the microprocessor 2 outputs a PWM wave to the high-frequency square wave generation circuit 3, the high-frequency square wave generation circuit 3 controls continuous on and off of the NMOS transistor Q1, so that continuous charge and discharge of the inductor L1 in the resonance circuit 4 are controlled, and finally half-wave oscillation of the ultrasonic atomizing sheet W is achieved. In the oscillation process, working current is collected by the current collection circuit 5 and sent to the microprocessor 2, so that the microprocessor 2 adjusts the frequency of the output PWM waves according to the magnitude of the working current, and finally the power of the ultrasonic atomizing sheet W is adjusted.

The half-wave drive circuit for the ultrasonic atomizing sheet shown in FIG. 1 has the following disadvantages:

In a drive cycle of the half-wave drive circuit, the effective drive time is only about 50% of the drive cycle, so the drive efficiency is low. In order to improve the atomizing power of the ultrasonic atomizing sheet, the boost module is required to be able to provide a relatively high and stable drive voltage (VCC), so the requirements for the boost module are relatively high, the loss of the boost module is large, and the power conversion efficiency is low.

Figure 2:
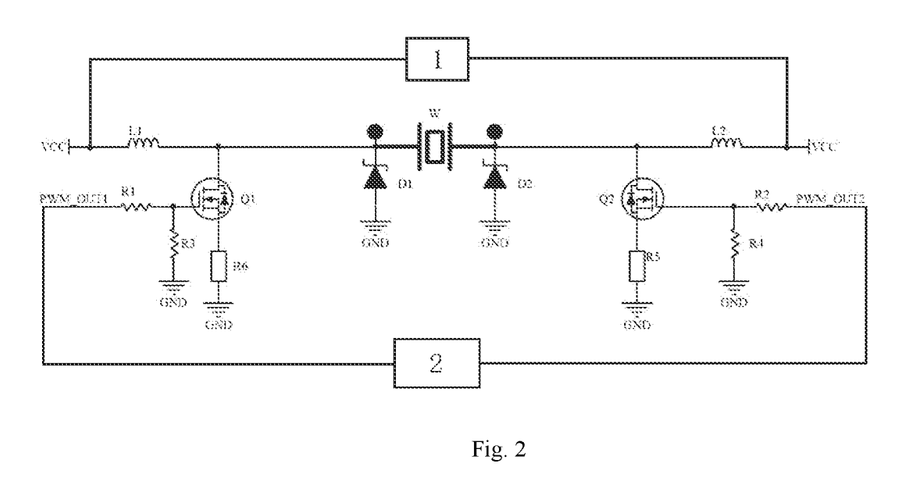
FIG. 2 is a structural diagram of a full-wave drive circuit for an ultrasonic atomizing sheet in the prior art.

As shown in FIG. 2, an existing full-wave drive circuit for an ultrasonic atomizing sheet includes a power module 1, a microprocessor 2, an NMOS transistor Q1, and an NMOS transistor Q2. A first output end of the microprocessor 2 is electrically connected to a gate of the NMOS transistor Q1 through a resistor R1, the gate of the NMOS transistor Q1 is grounded through a resistor R3, a source of the NMOS transistor Q1 is grounded through a resistor R6, a drain of the NMOS transistor Q1 is electrically connected to a first end of an inductor L1, and the first end of the inductor L1 is grounded through a Zener diode D1; a second output end of the microprocessor 2 is electrically connected to a gate of the NMOS transistor Q2 through a resistor R2, the gate of the NMOS transistor Q2 is grounded through a resistor R4, a source of the NMOS transistor Q2 is grounded through a resistor R5, a drain of the NMOS transistor Q2 is electrically connected to a first end of an inductor L2, and the first end of the inductor L2 is grounded through a Zener diode D2; the first end of the inductor L1 is electrically connected to one electrode of an ultrasonic atomizing sheet W, and the first end of the inductor L2 is electrically connected to the other electrode of the ultrasonic atomizing sheet W; and a second end of the inductor L1 and a second end of the inductor L2 are both electrically connected to an output end of the power module 1.

The working principle of the full-wave drive circuit for an ultrasonic atomizing sheet shown in FIG. 2 is: the microprocessor 2 outputs a path of PWM wave (PWM_OUT1) to control continuous on and off of the NMOS transistor Q1, so that continuous charge and discharge of the inductor L1 are controlled, and finally positive half-wave oscillation of the ultrasonic atomizing sheet W is achieved; and the microprocessor 2 outputs the other path of PWM wave (that is PWM_OUT2 which complements to PWM_OUT1) to control continuous on and off of the NMOS transistor Q2, so that continuous charge and discharge of the inductor L2 are controlled, and finally negative half-wave oscillation of the ultrasonic atomizing sheet W is achieved.

The full-wave drive circuit for the ultrasonic atomizing sheet shown in FIG. 2 has the following disadvantages:

Two half-wave drive circuits are required to work in a complementary form, that is, the microprocessor needs to output two drive signals "PWM_OUT1" and "PWM_OUT2" that work in a complementary form. If the duty cycles of the two signals do not match well, the positive half wave and the negative half wave may not be connected (for example, the positive half wave overlaps with the negative half wave, or one half wave lags behind the ideal wave), so the debugging of a drive program is very troublesome and the reliability is low.

SUMMARY OF THE INVENTION

In the two existing drive circuits for the ultrasonic atomizing sheet, the half-wave drive circuit has high requirements for the boost module, high loss of the boost module, and low power conversion efficiency; and the full-wave drive circuit is troublesome to debug and has low reliability. The objective of the present invention is to provide an improved full-wave drive circuit for an ultrasonic atomizing sheet and an ultrasonic electronic cigarette against the disadvantages of the two drive circuits in the prior art. Compared with the existing half-wave drive circuit for the ultrasonic atomizing sheet, the improved full-wave drive circuit for the ultrasonic atomizing sheet has low requirements for a boost module, reduces the loss of the boost module, and increases the power conversion efficiency; and compared with the existing full-wave drive circuit for the ultrasonic atomizing sheet, only one PWM drive signal is required, which facilitates debugging, and the output waveform is a complete and continuous sine wave signal, so there will be no connection problems such as waveform overlap or lag, and the reliability is higher.

In order to solve the above technical problems, the technical solution used by the present invention is as follows:

A full-wave drive circuit for an ultrasonic atomizing sheet, including a power module, a microprocessor, a high-frequency square wave generation circuit, an NMOS transistor and a resonance circuit; an output end of the power module is electrically connected to the resonance circuit; an output end of the microprocessor is electrically connected to a gate of the NMOS transistor through the high-frequency square wave generation circuit. The structure features of the full-wave drive circuit is that: the NMOS transistor and an ultrasonic atomizing sheet are both connected to the resonance circuit, and the resonance circuit is configured to convert, on the basis of the NMOS transistor, a voltage signal output by the high-frequency square wave generation circuit into a full-wave oscillation signal, so as to drive the ultrasonic atomizing sheet to perform full-wave oscillation.

With the above structure, after the PWM wave output by the microprocessor is amplified by the high-frequency square wave generation circuit, the resonance circuit finally converts the voltage signal output by the high-frequency square wave generation circuit into a full-wave oscillation signal on the basis of the on-off function of the NMOS transistor, so as to drive the ultrasonic atomizing sheet to perform full-wave oscillation.

Compared with the half-wave drive circuit for the ultrasonic atomizing sheet in the prior art, the present invention achieves full-wave oscillation, so the effective drive time in a drive cycle is 100% of the drive cycle, which is far greater than the half-wave drive circuit in the prior art with effective drive time of 50% of the drive cycle, and the present invention has high drive efficiency and high atomizing power of the ultrasonic atomizing sheet. Therefore, the output voltage of a boost module can be reduced under the same power condition, the requirements for the boost module are low, the loss of the boost module is reduced, and the power conversion efficiency is increased.

Compared with the full-wave drive circuit for the ultrasonic atomizing sheet in the prior art, the microprocessor of the present invention only needs to output one PWM drive signal, which facilitates debugging and which is a sine wave signal with a complete and continuous waveform, so the connection problems such as waveform overlap or lag are avoided, the reliability is higher, and the atomizing effect is better.

In a first solution, a source of the NMOS transistor is grounded; the resonance circuit includes a first inductor, a second inductor and a first capacitor; the output end of the power module is electrically connected to a positive electrode of the ultrasonic atomizing sheet through the first inductor and the second inductor in sequence, a negative electrode of the ultrasonic atomizing sheet is grounded, the first capacitor is connected between the positive electrode of the ultrasonic atomizing sheet and the ground, and a drain of the NMOS transistor is connected between the first inductor and the second inductor.

With the above structure, after the PWM wave output by the microprocessor is amplified by the high-frequency square wave generation circuit, continuous on and off of the NMOS transistor are controlled, and the boosted battery voltage is converted into a complete high-frequency sine wave by means of one power MOS transistor, two power inductors (the first inductor and the second inductor) and the first capacitor, to achieve full-wave oscillation of the ultrasonic atomizing sheet. Compared with the full-wave drive circuit for the ultrasonic atomizing sheet in the prior art, this circuit also has the following beneficial effects: one less power MOS transistor is used, and only one power MOS transistor is needed, which reduces the size, loss and cost.

In a second solution, a PMOS transistor is further included, and the resonance circuit includes a third inductor and a first capacitor; the output end of the power module is connected to the drain of the NMOS transistor; a gate of the PMOS transistor is connected to the gate of the NMOS transistor, and a drain of the PMOS transistor is grounded; a first end of the third inductor is connected between a source of the PMOS transistor and the source of the NMOS transistor, a second end of the third inductor is electrically connected to the positive electrode of the ultrasonic atomizing sheet, the negative electrode of the ultrasonic atomizing sheet is grounded, and the first capacitor is connected between the positive electrode of the ultrasonic atomizing sheet and the ground.

With the above structure, after the PWM wave output by the microprocessor is amplified by the high-frequency square wave generation circuit, continuous on and off of the NMOS transistor and the PMOS transistor are controlled, and the boosted battery voltage is converted into a complete high-frequency sine wave by means of two power MOS transistors (the NMOS transistor and the PMOS transistor), one power inductor and the first capacitor, to achieve full-wave oscillation of the ultrasonic atomizing sheet.

Further, the resonance circuit also includes a second capacitor, and the second capacitor and the second inductor are connected in series between the drain of the NMOS transistor and the positive electrode of the ultrasonic atomizing sheet.

Further, the resonance circuit also includes a second capacitor, and the second capacitor and the third inductor are connected in series between the source of the NMOS transistor and the positive electrode of the ultrasonic atomizing sheet.

The second capacitor has a relatively small capacitance value, and is mainly configured to reduce or eliminate the interference effect of parasitic capacitance in the ultrasonic atomizing sheet, so that the resonance effect is better.

Further, the resonance circuit also includes a transient voltage suppressor, and the transient voltage suppressor is connected between the positive electrode of the ultrasonic atomizing sheet and the ground.

The transient voltage suppressor is used for overvoltage protection of the ultrasonic atomizing sheet.

Further, a first resistor and a second resistor are also included, an output end of the high-frequency square wave generation circuit is electrically connected to the gate of the NMOS transistor through the first resistor, and the second resistor is connected between the gate of the NMOS transistor and the ground.

Further, a third capacitor is also included, one end of the third capacitor is connected between the first resistor and the second resistor, and the other end of the third capacitor is electrically connected to the gate of the NMOS transistor.

The third capacitor is a coupling capacitor, and is configured to filter out clutters at the front end of the gate of the NMOS transistor and the front end of the gate of the PMOS transistor.

As a preferred solution, the high-frequency square wave generation circuit includes a third resistor, a fourth capacitor and a square wave amplifier, the output end of the microprocessor is electrically connected to an input end of the square wave amplifier, the third resistor is connected between the output end of the microprocessor and the ground, a power end of the square wave amplifier is grounded through the fourth capacitor, and an output end of the square wave amplifier is the output end of the high-frequency square wave generation circuit.

The square wave amplifier is configured to amplify a PWM wave signal output by the microprocessor, and to control the continuous on and off of the NMOS transistor and the PMOS transistor.

In the first solution, a current collection circuit for collecting the working current between the source of the NMOS transistor and the ground is further included, and an output end of the current collection circuit is electrically connected to an input end of the microprocessor.

As a preferred solution, the current collection circuit includes a fourth resistor, a fifth resistor and a fifth capacitor, the fifth resistor is connected between the source of the NMOS transistor and the ground, the source of the NMOS transistor is grounded through the fourth resistor and the fifth capacitor in sequence, and the input end of the microprocessor is connected between the fourth resistor and the fifth capacitor.

In the second solution, a current collection circuit for collecting the working current between the drain of the PMOS transistor and the ground is further included, and an output end of the current collection circuit is electrically connected to the input end of the microprocessor.

As a preferred solution, the current collection circuit includes a fourth resistor, a fifth resistor and a fifth capacitor, the fifth resistor is connected between the drain of the PMOS transistor and the ground, the drain of the PMOS transistor is grounded through the fourth resistor and the fifth capacitor in sequence, and the input end of the microprocessor is connected between the fourth resistor and the fifth capacitor.

The current collection circuit is configured to collect the working current and send the same to the microprocessor, so that the microprocessor can adjust the frequency of the output PWM wave according to the magnitude of the working current, finally the power of the ultrasonic atomizing sheet can be adjusted, and the power output of the ultrasonic atomizing sheet is thereby stable and efficient.

As a preferred solution, the power module includes a battery and a boost module; an output end of the battery is electrically connected to an input end of the boost module; and an output end of the boost module is the output end of the power module.

Based on the same inventive concept, the present invention further provides an ultrasonic electronic cigarette, which is characterized by including the full-wave drive circuit for the ultrasonic atomizing sheet.

Compared with the prior art, the present invention overcomes the shortcomings of both the half-wave drive circuit for the ultrasonic atomizing sheet and the full-wave drive circuit for an ultrasonic atomizing sheet in the prior art, combines the advantages of the half-wave drive circuit for the ultrasonic atomizing sheet and the full-wave drive circuit for the ultrasonic atomizing sheet, and has the following beneficial effects:

First, compared with the half-wave drive circuit for the ultrasonic atomizing sheet in the prior art, the present invention achieves full-wave oscillation, so the effective drive time is 100% of a drive cycle, which is far greater than the half-wave drive circuit in the prior art with effective drive time of 50% of a drive cycle, and the present invention has high drive efficiency and high atomizing power of the ultrasonic atomizing sheet. Therefore, the output voltage of the boost module can be reduced under the same power condition, the requirements for the boost module are low, the loss of the boost module is reduced, and the power conversion efficiency is increased.

Second, compared with the full-wave drive circuit for the ultrasonic atomizing sheet in the prior art, the present invention uses one less power MOS transistor and only needs one power MOS transistor, which reduces the size, loss and cost; only one PWM drive signal is required, which facilitates debugging; and the output waveform is of a complete and continuous sine wave signal, so the connection problems such as waveform overlap or lag are avoided, the reliability is higher, and the atomizing effect is better.

BRIEF DESCRIPTION OF THE DRAWINGS

In FIGS. 3 to 6, 1—power module, 101—battery, 102—boost module, 2—microprocessor, 3—high-frequency square wave generation circuit, 4—resonance circuit, 5—current collection circuit, U1—square wave amplifier, L1—first inductor, L2—second inductor, L3—third inductor, C1—first capacitor, C2—second capacitor, C3—third capacitor, C4—fourth capacitor, C5—fifth capacitor, R1—first resistor, R2—second resistor, R3—third resistor, R4—fourth resistor, R5—fifth resistor, Q1—NMOS transistor, Q2—PMOS transistor, TVS1—transient voltage suppressor, W—ultrasonic atomizing sheet.

DETAILED DESCRIPTION OF THE EMBODIMENTS

Embodiment 1

Figure 3:
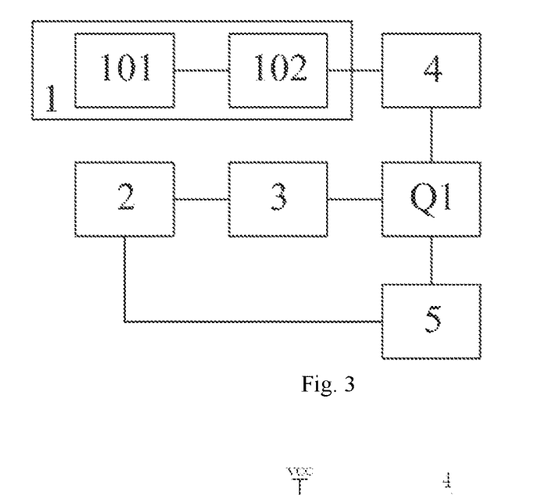
FIG. 3 is a circuit block diagram of Embodiment 1 of a full-wave drive circuit for an ultrasonic atomizing sheet according to the present invention.
Figure 4:
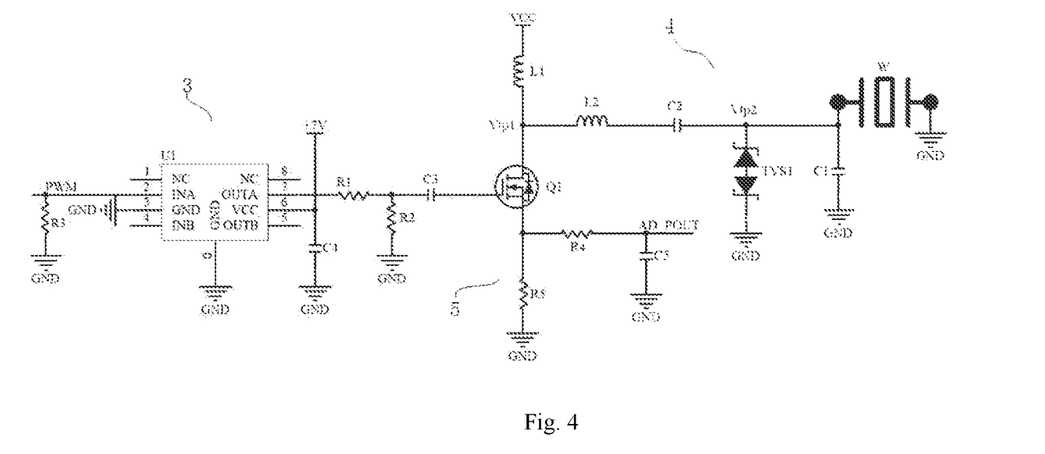
FIG. 4 is a simplified circuit diagram of FIG. 3.

As shown in FIGS. 3 and 4, a full-wave drive circuit for an ultrasonic atomizing sheet in an ultrasonic electronic cigarette includes a power module 1, a microprocessor 2, a high-frequency square wave generation circuit 3, an NMOS transistor Q1 and a resonance circuit 4; the power module 1 includes a battery 101 and a boost module 102; an output end of the battery 101 is electrically connected to the resonance circuit 4 through the boost module 102; an output end of the microprocessor 2 is electrically connected to a gate of the NMOS transistor Q1 through the high-frequency square wave generation circuit 3, and a source of the NMOS transistor Q1 is grounded; the resonance circuit 4 includes a first inductor L1, a second inductor L2 and a first capacitor C1; an output end of the boost module 102 is electrically connected to a positive electrode of the ultrasonic atomizing sheet W through the first inductor L1 and the second inductor L2 in sequence, a negative electrode of the ultrasonic atomizing sheet W is grounded, the first capacitor C1 is connected between the positive electrode of the ultrasonic atomizing sheet W and the ground, and a drain of the NMOS transistor Q1 is connected between the first inductor L1 and the second inductor L2.

In the first embodiment, the chip of the microprocessor 2 is ESM8BD10.

After the PWM wave output by the microprocessor 2 is amplified by the high-frequency square wave generation circuit 3, continuous on and off of the NMOS transistor Q1 are controlled, and the boosted battery voltage is converted into a complete high-frequency sine wave by one power MOS transistor (the NMOS transistor Q1), two power inductors (the first inductor L1 and the second inductor L2) and the first capacitor C1, to achieve full-wave oscillation of the ultrasonic atomizing sheet W.

The battery 101 supplies power to the high-frequency square wave generation circuit 3 and the resonance circuit 4 after the voltage of the battery 101 is boosted by the boost module 102. The battery 101 supplies power, and the voltage of the battery 101 is boosted by a boost chip in the boost module 102 to a voltage required by the resonance circuit 4, so the power module 1 has good versatility. In FIG. 4, VCC is connected to a voltage output end of the boost module 102.

The resonance circuit 4 further includes a second capacitor C2, and the second capacitor C2 and the second inductor L2 are connected in series between the drain of the NMOS transistor Q1 and the positive electrode of the ultrasonic atomizing sheet W. The second capacitor C2 has a relatively small capacitance value, and is mainly configured to reduce or eliminate the interference effect of parasitic capacitance in the ultrasonic atomizing sheet W, so that the resonance effect is better.

The resonance circuit 4 further includes a transient voltage suppressor TVS1, and the transient voltage suppressor TVS1 is connected between the positive electrode of the ultrasonic atomizing sheet W and the ground. The transient voltage suppressor TVS1 is used for overvoltage protection of the ultrasonic atomizing sheet W.

Working circuit for the ultrasonic atomizing sheet further includes a first resistor R1 and a second resistor R2, an output end of the high-frequency square wave generation circuit 3 is electrically connected to the gate of the NMOS transistor Q1 through the first resistor R1, and the second resistor R2 is connected between the gate of the NMOS transistor Q1 and the ground.

Working circuit for the ultrasonic atomizing sheet further includes a third capacitor C3, one end of the third capacitor C3 is connected between the first resistor R1 and the second resistor R2, and the other end of the third capacitor C3 is electrically connected to the gate of the NMOS transistor Q1. The third capacitor C3 is a coupling capacitor, and is configured to filter out the clutter at the front end of the gate of the NMOS transistor Q1.

The high-frequency square wave generation circuit 3 includes a third resistor R3, a fourth capacitor C4 and a square wave amplifier U1, the output end of the microprocessor 2 is electrically connected to an input end of the square wave amplifier U1, the third resistor R3 is connected between the output end of the microprocessor 2 and the ground, a power end of the square wave amplifier U1 is grounded through the fourth capacitor C4, and an output end of the square wave amplifier U1 is the output end of the high-frequency square wave generation circuit 3.

The square wave amplifier U1 is configured to amplify a PWM wave signal output by the microprocessor 2, and to control the continuous on and off of the NMOS transistor Q1. In the first embodiment, the model of the square wave amplifier U1 is SDM48000.

The working circuit for the ultrasonic atomizing sheet further includes a current collection circuit 5 for collecting the working current between the source of the NMOS transistor Q1 and the ground, and an output end of the current collection circuit 5 is electrically connected to the input end of the microprocessor 2. The current collection circuit 5 is configured to collect the working current and send the same to the microprocessor 2, so that the microprocessor 2 can adjust the frequency of the output PWM wave according to the magnitude of the working current, finally the power of the ultrasonic atomizing sheet W can be adjusted, and the power output of the ultrasonic atomizing sheet W is thereby stable and efficient.

The current collection circuit 5 includes a fourth resistor R4, a fifth resistor R5 and a fifth capacitor C5, the fifth resistor R5 is connected between the source of the NMOS transistor Q1 and the ground, the source of the NMOS transistor Q1 is grounded through the fourth resistor R4 and the fifth capacitor C5 in sequence, and the input end of the microprocessor 2 is connected between the fourth resistor R4 and the fifth capacitor C5.

The battery 101 is a rechargeable battery, such as a rechargeable lithium battery. Correspondingly, the power module 1 further includes a charging circuit and a discharging protection circuit. The structures of the charging circuit and the discharging protection circuit are not shown in the drawings, which does not affect the understanding and implementation of the present invention by those skilled in the art.

The full-wave oscillation principle of the ultrasonic atomizing sheet in the present invention is as follows:

The microprocessor 2 outputs a PWM wave to the high-frequency square wave generation circuit 3, and the PWM wave is amplified by the high-frequency square wave generation circuit 3, and the amplified PWM wave is used to control continuous on and off of the NMOS transistor Q1.

When the NMOS transistor Q1 is turned off, the voltage output end VCC of the boost module 102 charges the first inductor L1, the second inductor L2 and the first capacitor C1, then VCC>Vtp1>Vtp2, and the drive waveform at Vtp2 is a positive half wave of a sine wave. When the NMOS transistor Q1 is turned on, Vtp1 is instantly pulled down to approximately 0 V, then Vtp1>Vtp2, a negative voltage will be generated at Vtp2, and the drive waveform at Vtp2 is a negative half wave of the sine wave. Therefore, as long as the PWM wave of the drive signal is of a square wave signal with a duty cycle of 50%, a complete and continuous sine wave as a drive waveform is obtained at Vtp2.

Because the Vtp2 is directly connected to the positive electrode of the ultrasonic atomizing sheet W, and the negative electrode of the ultrasonic atomizing sheet W is connected to the negative electrode of the power module 1, a complete high-frequency sine wave oscillation can be obtained at two ends of the ultrasonic atomizing sheet W, which allows the ultrasonic atomizing sheet W to oscillate and makes the ultrasonic electronic cigarette to emit smoke.

Embodiment 2

Figure 5:
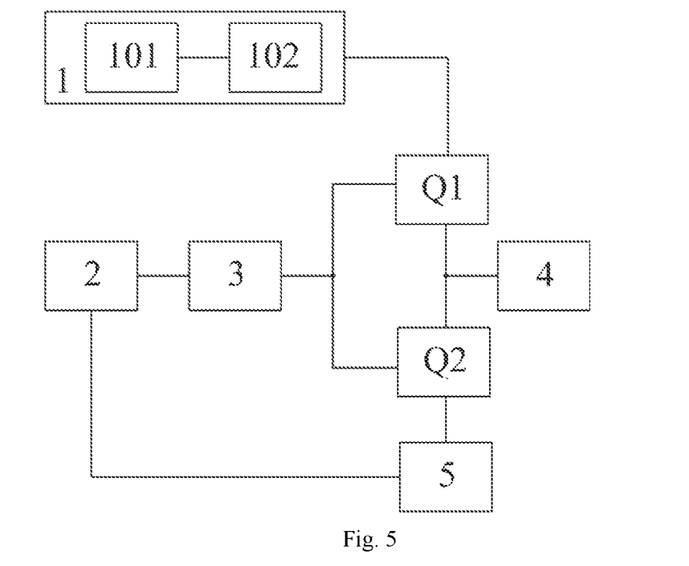
FIG. 5 is a circuit block diagram of Embodiment 2 of a full-wave drive circuit for an ultrasonic atomizing sheet according to the present invention.
Figure 6:
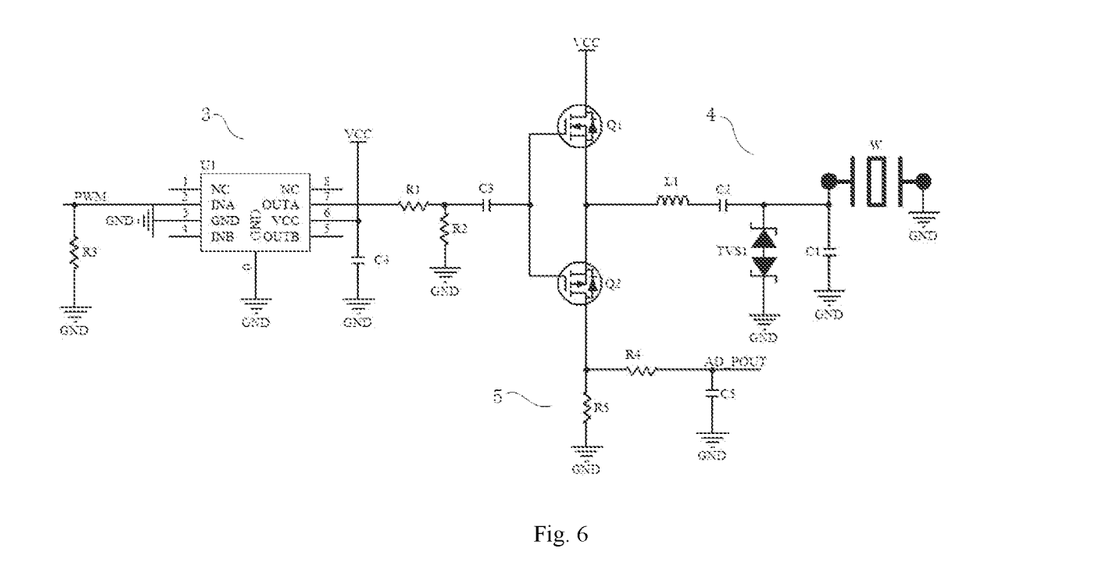
FIG. 6 is a simplified circuit diagram of FIG. 5.

As shown in FIGS. 5 and 6, a full-wave drive circuit for an ultrasonic atomizing sheet in an ultrasonic electronic cigarette includes a power module 1, a microprocessor 2, a high-frequency square wave generation circuit 3, an NMOS transistor Q1 and a resonance circuit 4; the power module 1 includes a battery 101 and a boost module 102; an output end of the battery 101 is electrically connected to an input end of the boost module 102; an output end of the microprocessor 2 is electrically connected to a gate of the NMOS transistor Q1 through the high-frequency square wave generation circuit 3; a PMOS transistor Q2 is further included, and the resonance circuit 4 includes a third inductor L3 and a first capacitor C1; an output end of the boost module 102 is connected to a drain of the NMOS transistor Q1; a gate of the PMOS transistor Q2 is connected to the gate of the NMOS transistor Q1, and a drain of the PMOS transistor Q2 is grounded; a first end of the third inductor L3 is connected between a source of the PMOS transistor Q2 and a source of the NMOS transistor Q1, a second end of the third inductor L3 is electrically connected to a positive electrode of the ultrasonic atomizing sheet W, a negative electrode of the ultrasonic atomizing sheet W is grounded, and the first capacitor C1 is connected between the positive electrode of the ultrasonic atomizing sheet W and the ground.

In the second embodiment, the chip model of the microprocessor 2 is ESM8BD10.

After the PWM wave output by the microprocessor 2 is amplified by the high-frequency square wave generation circuit 3, continuous on and off of the NMOS transistor Q1 and the PMOS transistor Q2 are controlled, and the boosted battery voltage is converted into a complete high-frequency sine wave by two power MOS transistors (the NMOS transistor Q1 and the PMOS transistor Q2), one power inductor (the third inductor L3) and the first capacitor C1, to achieve full-wave oscillation of the ultrasonic atomizing sheet W.

The battery 101 supplies power to the high-frequency square wave generation circuit 3 and the resonance circuit 4 after being boosted by the boost module 102. The battery 101 supplies power, and the voltage of the battery 101 is boosted by a boost chip in the boost module 102 to a voltage required by the resonance circuit 4, so the power module 1 has good versatility. In FIG. 6, VCC is connected to a voltage output end of the boost module 102.

The resonance circuit 4 further includes a second capacitor C2, and the second capacitor C2 and the third inductor L3 are connected in series between the source of the NMOS transistor Q1 and the positive electrode of the ultrasonic atomizing sheet W. The second capacitor C2 has a relatively small capacitance value, and is mainly configured to reduce or eliminate the interference effect of parasitic capacitance in the ultrasonic atomizing sheet W, so that the resonance effect is better.

The resonance circuit 4 further includes a transient voltage suppressor TVS1, and the transient voltage suppressor TVS1 is connected between the positive electrode of the ultrasonic atomizing sheet W and the ground. The transient voltage suppressor TVS1 is used for overvoltage protection of the ultrasonic atomizing sheet W.

The working circuit for the ultrasonic atomizing sheet further includes a first resistor R1 and a second resistor R2, an output end of the high-frequency square wave generation circuit 3 is electrically connected to the gate of the NMOS transistor Q1 through the first resistor R1, and the second resistor R2 is connected between the gate of the NMOS transistor Q1 and the ground.

The working circuit for the ultrasonic atomizing sheet further includes a third capacitor C3, one end of the third capacitor C3 is connected between the first resistor R1 and the second resistor R2, and the other end of the third capacitor C3 is electrically connected to the gate of the NMOS transistor Q1. The third capacitor C3 is a coupling capacitor, and is configured to filter out clutters at the front ends of the gate of the NMOS transistor Q1 and the gate of the PMOS transistor Q2.

The high-frequency square wave generation circuit 3 includes a third resistor R3, a fourth capacitor C4 and a square wave amplifier U1, the output end of the microprocessor 2 is electrically connected to an input end of the square wave amplifier U1, the third resistor R3 is connected between the output end of the microprocessor 2 and the ground, a power end of the square wave amplifier U1 is grounded through the fourth capacitor C4, and an output end of the square wave amplifier U1 is the output end of the high-frequency square wave generation circuit 3.

The square wave amplifier U1 is configured to amplify a PWM wave signal output by the microprocessor 2, and to control the continuous on and off of the NMOS transistor Q1 and the PMOS transistor Q2.

In the second embodiment, the model of the square wave amplifier U1 is SDM48000.

The working circuit for the ultrasonic atomizing sheet further includes a current collection circuit 5 for collecting the working current between the drain of the PMOS transistor Q2 and the ground, and an output end of the current collection circuit 5 is electrically connected to the input end of the microprocessor 2. The current collection circuit 5 is configured to collect the working current and send the same to the microprocessor 2, so that the microprocessor 2 can adjust the frequency of the output PWM wave according to the magnitude of the working current, finally the power of the ultrasonic atomizing sheet W can be adjusted, and the power output of the ultrasonic atomizing sheet W is thereby stable and efficient.

The current collection circuit 5 includes a fourth resistor R4, a fifth resistor R5 and a fifth capacitor C5, the fifth resistor R5 is connected between the drain of the PMOS transistor Q2 and the ground, the drain of the PMOS transistor Q2 is grounded through the fourth resistor R4 and the fifth capacitor C5 in sequence, and the input end of the microprocessor 2 is connected between the fourth resistor R4 and the fifth capacitor C5.

The battery 101 is a rechargeable battery, such as a rechargeable lithium battery. Correspondingly, the power module 1 further includes a charging circuit and a discharging protection circuit. The structures of the charging circuit and the discharging protection circuit are not shown in the drawings, which does not affect the understanding and implementation of the present invention by those skilled in the art.

The full-wave oscillation principle of the ultrasonic atomizing sheet in the present invention is as follows:

The microprocessor 2 outputs a PWM wave to the high-frequency square wave generation circuit 3, and the PWM wave amplified by the high-frequency square wave generation circuit 3, and the amplified PWM wave is used to control continuous on and off of the NMOS transistor Q1 and the PMOS transistor Q2.

When the drive signal provided by the square wave amplifier U1 is at a high level, the NMOS transistor Q1 is turned on while the PMOS transistor Q2 is turned off, and the VCC output by the power module 1 charges the third inductor L3 and the first capacitor C1 through the NMOS transistor Q1; when the drive signal provided by the square wave amplifier U1 is at a low level, the NMOS transistor Q1 is turned off while the PMOS transistor Q2 is turned on, and the third inductor L3 and the first capacitor C1 are discharged through the PMOS transistor Q2; and when the PWM signal controls the continuous on and off of the NMOS transistor Q1 and the PMOS transistor Q2, a complete and continuous sine wave as a drive waveform is obtained. The amplified signal is connected to the positive electrode of the ultrasonic atomizing sheet W, and the negative electrode of the ultrasonic atomizing sheet W is connected to the negative electrode of the power module 1, so a complete high-frequency sine wave oscillation can be obtained at two ends of the ultrasonic atomizing sheet W, which allows the ultrasonic atomizing sheet W to oscillate and make the ultrasonic electronic cigarette to emit smoke.

The embodiments of the present invention are described above with reference to the drawings, but the present invention is not limited to the specific embodiments. The specific embodiments described above are merely illustrative but not restrictive. Many forms may also be made by those of ordinary skill in the art under the enlightenment of the present invention without departing from the purpose of the present invention and the scope of the claims, and these forms fall into the scope of the present invention.

The invention claimed is:

1. A full-wave drive circuit for an ultrasonic atomizing sheet, comprising a power module (1), a microprocessor (2), a high-frequency square wave generation circuit (3), an NMOS transistor (Q1) and a resonance circuit (4); an output end of the power module (1) is electrically connected to the resonance circuit (4); an output end of the microprocessor (2) is electrically connected to a gate of the NMOS transistor (Q1) through the high-frequency square wave generation circuit (3), wherein the NMOS transistor (Q1) and an ultrasonic atomizing sheet (W) are both connected to the resonance circuit (4), and the resonance circuit (4) is configured to convert, based on the NMOS transistor (Q1), a voltage signal output by the high-frequency square wave generation circuit (3) into a full-wave oscillation signal, so as to drive the ultrasonic atomizing sheet (W) to perform full-wave oscillation.

2. The full-wave drive circuit for the ultrasonic atomizing sheet according to claim 1, wherein a source of the NMOS transistor (Q1) is grounded; the resonance circuit (4) comprises a first inductor (L1), a second inductor (L2) and a first capacitor (C1); the output end of the power module (1) is electrically connected to a positive electrode of the ultrasonic atomizing sheet (W) through the first inductor (L1) and the second inductor (L2) in sequence, a negative electrode of the ultrasonic atomizing sheet (W) is grounded, the first capacitor (C1) is connected between the positive electrode of the ultrasonic atomizing sheet (W) and the ground, and a drain of the NMOS transistor (Q1) is connected between the first inductor (L1) and the second inductor (L2).

3. The full-wave drive circuit for the ultrasonic atomizing sheet according to claim 1, further comprising a PMOS transistor (Q2), wherein the resonance circuit (4) comprises a first inductor (L1) and a first capacitor (C1); the output end of the power module (1) is connected to the drain of the NMOS transistor (Q1); a gate of the PMOS transistor (Q2) is connected to the gate of the NMOS transistor (Q1), and a drain of the PMOS transistor (Q2) is grounded; a first end of the first inductor (L1) is connected between a source of the PMOS transistor (Q2) and the source of the NMOS transistor (Q1), a second end of the first inductor (L1) is electrically connected to a positive electrode of the ultrasonic atomizing sheet (W), a negative electrode of the ultrasonic atomizing sheet (W) is grounded, and the first capacitor (C1) is connected between the positive electrode of the ultrasonic atomizing sheet (W) and the ground.

4. The full-wave drive circuit for the ultrasonic atomizing sheet according to claim 2, wherein the resonance circuit (4) further comprises a second capacitor (C2), and the second capacitor (C2) and the second inductor (L2) are connected in series between the drain of the NMOS transistor (Q1) and the positive electrode of the ultrasonic atomizing sheet (W).

5. The full-wave drive circuit for the ultrasonic atomizing sheet according to claim 3, wherein the resonance circuit (4) further comprises a second capacitor (C2), and the second capacitor (C2) and the first inductor (L1) are connected in series between the source of the NMOS transistor (Q1) and the positive electrode of the ultrasonic atomizing sheet (W).

6. The full-wave drive circuit for the ultrasonic atomizing sheet according to claim 2, wherein the resonance circuit (4) further comprises a transient voltage suppressor (TVS1), and the transient voltage suppressor (TVS1) is connected between the positive electrode of the ultrasonic atomizing sheet (W) and the ground.

7. The full-wave drive circuit for the ultrasonic atomizing sheet according to claim 2, further comprising a first resistor (R1) and a second resistor (R2), wherein an output end of the high-frequency square wave generation circuit (3) is electrically connected to the gate of the NMOS transistor (Q1) through the first resistor (R1), and the second resistor (R2) is connected between the gate of the NMOS transistor (Q1) and the ground.

8. The full-wave drive circuit for the ultrasonic atomizing sheet according to claim 7, further comprising a third capacitor (C3), wherein one end of the third capacitor (C3) is connected between the first resistor (R1) and the second resistor (R2), and the other end of the third capacitor (C3) is electrically connected to the gate of the NMOS transistor (Q1).

9. The full-wave drive circuit for the ultrasonic atomizing sheet according to claim 2, wherein the high-frequency square wave generation circuit (3) comprises a third resistor (R3), a fourth capacitor (C4) and a square wave amplifier (U1), the output end of the microprocessor (2) is electrically connected to an input end of the square wave amplifier (U1), the third resistor (R3) is connected between the output end of the microprocessor (2) and the ground, a power end of the square wave amplifier (U1) is grounded through the fourth capacitor (C4), and an output end of the square wave amplifier (U1) is the output end of the high-frequency square wave generation circuit (3).

10. The full-wave drive circuit for the ultrasonic atomizing sheet according to claim 2, further comprising a current collection circuit (5) for collecting the working current between the source of the NMOS transistor (Q1) and the ground, wherein an output end of the current collection circuit (5) is electrically connected to an input end of the microprocessor (2).

11. The full-wave drive circuit for the ultrasonic atomizing sheet according to claim 10, wherein the current collection circuit (5) comprises a fourth resistor (R4), a fifth resistor (R5) and a fifth capacitor (C5), the fifth resistor (R5) is connected between the source of the NMOS transistor (Q1) and the ground, the source of the NMOS transistor (Q1) is grounded through the fourth resistor (R4) and the fifth capacitor (C5) in sequence, and the input end of the microprocessor (2) is connected between the fourth resistor (R4) and the fifth capacitor (C5).

12. The full-wave drive circuit for the ultrasonic atomizing sheet according to claim 3, further comprising a current collection circuit (5) for collecting the working current between the drain of the PMOS transistor (Q2) and the ground, wherein an output end of the current collection circuit (5) is electrically connected to an input end of the microprocessor (2).

13. The full-wave drive circuit for the ultrasonic atomizing sheet according to claim 12, wherein the current collection circuit (5) comprises a fourth resistor (R4), a fifth resistor (R5) and a fifth capacitor (C5), the fifth resistor (R5) is connected between the drain of the PMOS transistor (Q2) and the ground, the drain of the PMOS transistor (Q2) is grounded through the fourth resistor (R4) and the fifth capacitor (C5) in sequence, and the input end of the microprocessor (2) is connected between the fourth resistor (R4) and the fifth capacitor (C5).

14. The full-wave drive circuit for the ultrasonic atomizing sheet according to claim 1, wherein the power module (1) comprises a battery (101) and a boost module (102); an output end of the battery (101) is electrically connected to an input end of the boost module (102); and an output end of the boost module (102) is the output end of the power module (1).

15. An ultrasonic electronic cigarette, comprising the full-wave drive circuit for the ultrasonic atomizing sheet according to claim 1.

16. The full-wave drive circuit for the ultrasonic atomizing sheet according to claim 3, wherein the resonance circuit (4) further comprises a transient voltage suppressor (TVS1), and the transient voltage suppressor (TVS1) is connected between the positive electrode of the ultrasonic atomizing sheet (W) and the ground.

17. The full-wave drive circuit for the ultrasonic atomizing sheet according to claim 3, further comprising a first resistor (R1) and a second resistor (R2), wherein an output end of the high-frequency square wave generation circuit (3) is electrically connected to the gate of the NMOS transistor (Q1) through the first resistor (R1), and the second resistor (R2) is connected between the gate of the NMOS transistor (Q1) and the ground.

18. The full-wave drive circuit for the ultrasonic atomizing sheet according to claim 3, wherein the high-frequency square wave generation circuit (3) comprises a third resistor (R3), a fourth capacitor (C4) and a square wave amplifier (U1), the output end of the microprocessor (2) is electrically connected to an input end of the square wave amplifier (U1), the third resistor (R3) is connected between the output end of the microprocessor (2) and the ground, a power end of the square wave amplifier (U1) is grounded through the fourth capacitor (C4), and an output end of the square wave amplifier (U1) is the output end of the high-frequency square wave generation circuit (3).

\* \* \* \* \*